(12) United States Patent
Cheon et al.

(10) Patent No.: US 8,904,870 B2
(45) Date of Patent: Dec. 9, 2014

(54) DEVICE FOR PREDICTION UNDERGROUND BEHAVIOR BY USING ACOUSTIC EMISSION SENSOR AND PRODUCING METHOD THEREOF

(75) Inventors: Dae-Sung Cheon, Daejeon (KR); Yong-Bok Jung, Daejon (KR); Eui-Sub Park, Yongin-si (KR); Dae-Gee Huh, Daejeon (KR)

(73) Assignee: Korea Institute of Geoscience and Mineral Resources, Yuseong-gu, Daejeon (KR)

( * ) Notice: Subject to any disclaimer, the term of this patent is extended or adjusted under 35 U.S.C. 154(b) by 226 days.

(21) Appl. No.: 13/600,650

(22) Filed: Aug. 31, 2012

(65) Prior Publication Data

US 2013/0298677 A1    Nov. 14, 2013

(30) Foreign Application Priority Data

May 10, 2012    (KR) .................. 10-2012-0049453

(51) Int. Cl.
*E21B 49/00* (2006.01)
*G01V 1/40* (2006.01)

(52) U.S. Cl.
USPC ........................... 73/587; 73/152.58

(58) Field of Classification Search
USPC ...................... 73/587, 594, 152.58
See application file for complete search history.

(56) References Cited

U.S. PATENT DOCUMENTS

| 5,798,981 | A  | * | 8/1998 | Littlejohn et al. | ............... 367/13 |
| 8,353,205 | B2 | * | 1/2013 | Cheon et al. | ............... 73/152.58 |
| 2010/0206078 | A1 | * | 8/2010 | Cheon et al. | ............... 73/587 |
| 2011/0219867 | A1 | | 9/2011 | Cheon et al. | |

FOREIGN PATENT DOCUMENTS

JP    08-062337    8/1996
KR    10-2009-0117402    11/2009

* cited by examiner

*Primary Examiner* — Peter Macchiarolo
*Assistant Examiner* — Rose M Miller
(74) *Attorney, Agent, or Firm* — Davis & Bujold, PLLC; Michael J. Bujold

(57) ABSTRACT

Provided is a device for predicting an underground behavior by using an acoustic emission (AE) sensor, including: a waveguide rod having an elongated end to be inserted in a borehole; a plurality of acoustic emission sensors mounted on different positions of the waveguide rod; a wrapping layer configured to cover a circumferential surface of the waveguide rod such that a gap is formed between the waveguide rod and the wrapping layer; an acoustic emission generating layer filled into the gap and being homogeneous along a direction of the waveguide rod; and a grouting layer configured to fix the waveguide rod in the borehole.

13 Claims, 4 Drawing Sheets

DEVICE FOR PREDICTION UNDERGROUND BEHAVIOR BY USING ACOUSTIC EMISSION SENSOR AND PRODUCING METHOD THEREOF

RELATED APPLICATIONS

This application claims priority to Korean Patent Application No. 10-2012-0049453, filed on May 10, 2012, which is herein incorporated by reference in its entirety.

BACKGROUND

1. Field

The following description relates to a device for predicting underground behavior by using an acoustic emission (AE) sensor that monitors an underground dynamic state or behavior by inserting a waveguide rod with a reliable and superior acoustic emission sensor into an underground, and predicts a possibility of collapse, and a producing method thereof.

2. Description of the Related Art

Regional torrential rains, super typhoon, flood, etc. due to climatic change cause frequent landslides, losses of a slope and collapses, thereby requiring development of technology for preventing geological disasters.

It is required to follow a process of extracting a behavior of bedrock or a ground as a proper signal in order to predict or estimate stability of a disintegrable target land and then analyzing the behavior. A sensor is needed to obtain a signal according to the behavior and most precisely send an environment inside the bedrock or the ground. General technologies or devices used for predicting collapse of the ground structure include a displacement measuring method using an underground displacement gauge, underground clinometers, or Global Positioning Systems (GPS), a measuring method of fluctuations of ground-water level using a piezometer, and a stress measuring method using a load gauge.

However, since a variance is very small until the collapse of the ground or the bedrock and it is not easy to find a feature in occurrence tendency of stress or variance, it is difficult to notice a sign of collapse by the displacement or stress measuring methods. An acoustic emission sensor is prepared to solve the difficulty in predicting the sign of collapse. The acoustic emission sensor uses a microscopic breaking sound generated inside an object at an early stage that the object is broken as a signal. The acoustic emission (AE) is an elastic wave generated when deformation energy accumulated in materials is suddenly emitted. There is a general tendency that generation of the acoustic emission remarkably increases before a full-scale collapse.

JP Patent Laid-Open No. 1996-062337, which is related to a device for predicting a behavior in a ground or bedrock by using AE, discloses a method for inserting a waveguide filling an acoustic emission generating layer into a borehole. However, the waveguide is spaced apart from the inner wall of the borehole and there is a disadvantage that the change of the ground stress is not sufficiently transferred to the waveguide.

KR Patent Publication No. 2009-0117402 discloses a method of inserting a metal rod for transferring AE into a borehole and fixing the metal rod using cement. However, in a grouting process, there is a possibility that non-homogeneity of materials increases due to change of proportions according to cement sieving, i.e., depth. Accordingly, acoustic emission is differently generated to cause deterioration of reliability in measurement values.

SUMMARY

An embodiment of the present invention is directed to providing a device for predicting underground behavior by using a reliable and superior acoustic emission (AE) sensor that detects a behavior of an underground or a bedrock structure and predicts possibility of collapse.

Another embodiment of the present invention is directed to increase an yield of acoustic emission by a pillar itself for a waveguide and minimize a sieving possibility according to depths in a middle of installation.

To achieve the embodiment of the present invention, provided is a device for predicting an underground behavior by using an acoustic emission (AE) sensor, including: a waveguide rod having an elongated end to be inserted in a borehole; a plurality of acoustic emission sensors mounted on different positions of the waveguide rod; a wrapping layer configured to cover a circumferential surface of the waveguide rod such that a gap is formed between the waveguide rod and the wrapping layer; an acoustic emission generating layer filled into the gap and being homogeneous along a direction of the waveguide rod; and a grouting layer configured to fix the waveguide rod in the borehole.

The waveguide rod may be formed of a metal material.

The acoustic emission sensor may include a first acoustic emission sensor disposed on an upper end of the waveguide rod and a second acoustic emission sensor disposed on a lower end of the waveguide rod.

The wrapping layer may be formed of a resin based pipe.

The wrapping layer may be sealed to block a lower end portion of the waveguide rod and may have an open type upper end.

The acoustic emission generating layer may be formed of epoxy resin.

The grouting layer may be formed of cement.

Further, provided is a device for predicting an underground behavior by using an acoustic emission, including: a waveguide rod having an elongated end to be inserted in a borehole; a first acoustic emission sensor mounted on an upper end of the waveguide rod and a second acoustic emission sensor mounted on an lower end of the waveguide rod; a cured homogeneous acoustic emission generating layer disposed to cover a circumferential surface of the waveguide rod; and a grouting layer formed on an outside of the waveguide rod to fix the waveguide rod.

The acoustic emission generating layer may be formed of epoxy resin and the grouting layer may be formed of cement.

Further, provided is a producing method of a device for predicting an underground behavior by using an acoustic emission (AE), including the steps of: producing a waveguide rod having an elongated end to be inserted in a borehole; mounting a plurality of acoustic emission sensors on different positions of the waveguide rod; disposing a wrapping layer to cover a circumferential surface of the waveguide rod such that a gap is formed between the waveguide rod and the wrapping layer; filling and curing a homogeneous acoustic emission generating layer in the formed gap; and forming a grouting layer formed on an outside of the wrapping layer to fix the waveguide rod to the borehole.

The step of disposing the wrapping layer to cover the circumferential surface of the waveguide rod may further include the step of: sealing a lower end of the wrapping layer to block a leakage of the acoustic emission generating layer.

The step of mounting the plurality of acoustic emission sensors on different positions of the waveguide rod may be preparing a recess on each of a lower end and an upper end of the waveguide rod; mounting a first acoustic emission sensor to a recess of the upper end; and mounting a second acoustic emission sensor to a recess of the lower end.

The step of filling and curing the homogeneous acoustic emission generating layer in the formed gap and the step of forming the grouting layer formed on the outside of the waveguide rod to fix the waveguide rod to the borehole, may further include the step of: removing the wrapping layer.

DETAILED DESCRIPTION

Hereinafter, a device for predicting underground behavior by using an acoustic emission sensor and a producing method thereof will be described in detail with reference to the accompanying drawings.

Figure 1:
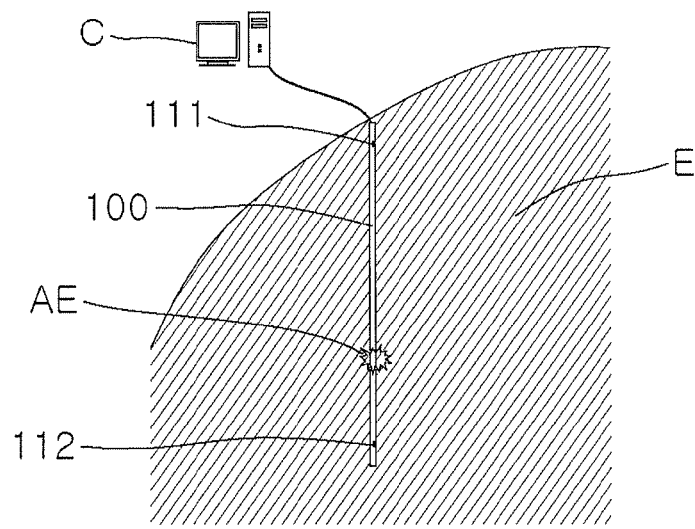
FIG. 1 is a cross-sectional view that schematically shows a state that an underground behavior predicting device 100 using an acoustic emission (AE) sensor in accordance with an exemplary embodiment is installed under a ground.

FIG. 1 is a cross-sectional view that schematically shows a state that an underground behavior predicting device 100 using an acoustic emission (AE) sensor in accordance with an exemplary embodiment is installed under a ground.

As shown in FIG. 1, the underground behavior predicting device 100 using an acoustic emission sensor of a pillar shape is installed to measure or predict a behavior of bedrock or a ground of a target region (E). The behavior predicting device 100 includes a plurality of acoustic emission sensors 111 and 112. The acoustic emission sensor 111 and 112 are disposed in different positions and generating positions of the acoustic emission are determined based on comparison of the positions. That is, when shear force or tension is generated in a specific underground position, a change of the stress in that position may generate acoustic emission around a shear breaking face or a tension breaking face. Since an acoustic emission signal easily dissipates, a member such as a rigid pillar with a superior waveguide property is used such that the acoustic emission signal reaches the sensor. Although the acoustic emissions are generated in the same positions, they have different reaching times to sensors 111 and 112. Accordingly, the positions that the acoustic emissions are generated are precisely calculated by using the time differences.

The behavior predicting device 100 buried underground is connected via a computer or a monitoring device C on the ground. The behavior predicting device 100 monitors the acoustic emission signal generated underground in real time and predicts a behavior or a collapse possibility to be generated in the underground of a target region E based on the signal.

Figure 2:
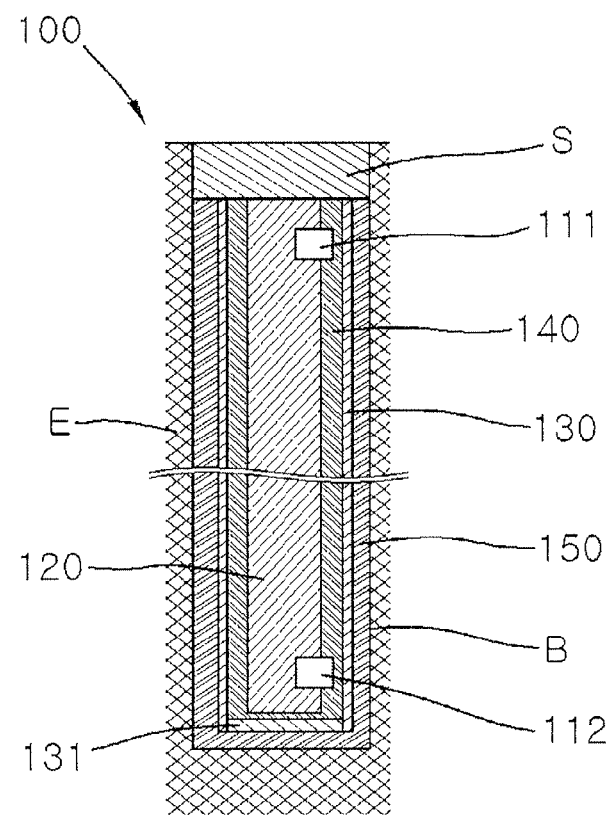
FIG. 2 is a cross-sectional view showing the underground behavior predicting device 100 using the acoustic emission sensor in accordance with an exemplary embodiment.

FIG. 2 is a cross-sectional view showing the underground behavior predicting device 100 using the acoustic emission sensor in accordance with an exemplary embodiment.

As shown in FIG. 2, the underground behavior predicting device 100 using an acoustic emission sensor includes a waveguide rod 120, a first acoustic emission sensor 111 and a second acoustic emission sensor 112, a wrapping layer 130, an acoustic emission generating layer 140 and a grouting layer 150. The first acoustic emission sensor 111 and the second acoustic emission sensor 112 are respectively adhered to an upper end and a lower end of the waveguide rod 120. The above-mentioned elements will be described in detail.

The waveguide rod 120 has an elongated end to be inserted into a borehole B. A weight may be connected to the waveguide rod 120 according to the depth of the borehole B. For materials, the waveguide rod 120 may be formed of a metal material such as a stainless steel that improves durability and is good at transferring wave.

The first acoustic emission sensor 111 and the second acoustic emission sensor 112 prepare a recess at an upper end of the waveguide rod 120 and are adhered to the recess to be installed. Materials such as vacuum grease may be applied to improve wave transmissibility.

Each of the first acoustic emission sensor 111 and the second acoustic emission sensor 112 may be installed in a radius direction with respect to the waveguide rod 120. Accordingly, the first acoustic emission sensor 111 and the second acoustic emission sensor 112 may be slightly protruded to the waveguide rod 120. The inside of the protruded first and second acoustic emission sensors 111 and 112 may be completely covered by the acoustic emission generating layer 140 in a state that they are disposed in the inside of the wrapping layer 130.

The wrapping layer 130 may be formed of a resin based pipe. A pipe formed of polyvinyl chloride (PVC) resin that has a superior workability and easily generates acoustic emission may be used for the wrapping layer. The wrapping layer 130 may be removed in the middle of processes as described below.

For example, a material such as epoxy resin that has a superior brittle may be used for the acoustic emission generating layer 140.

The grouting layer 150 for fixing the waveguide rod 120 to a borehole E is formed at an outer side of the wrapping layer 130. Conventional materials such as cement may be used for the grouting layer 150. However, when only the grouting layer 150 is used as a place for generating acoustic emission, an error may occur due to sieving actions. On the other hand, in this exemplary embodiment, homogeneity of the materials is secured by the acoustic emission generating layer 140 and the wrapping layer 130 and such homogeneity does not change in a curing process.

Figure 3:
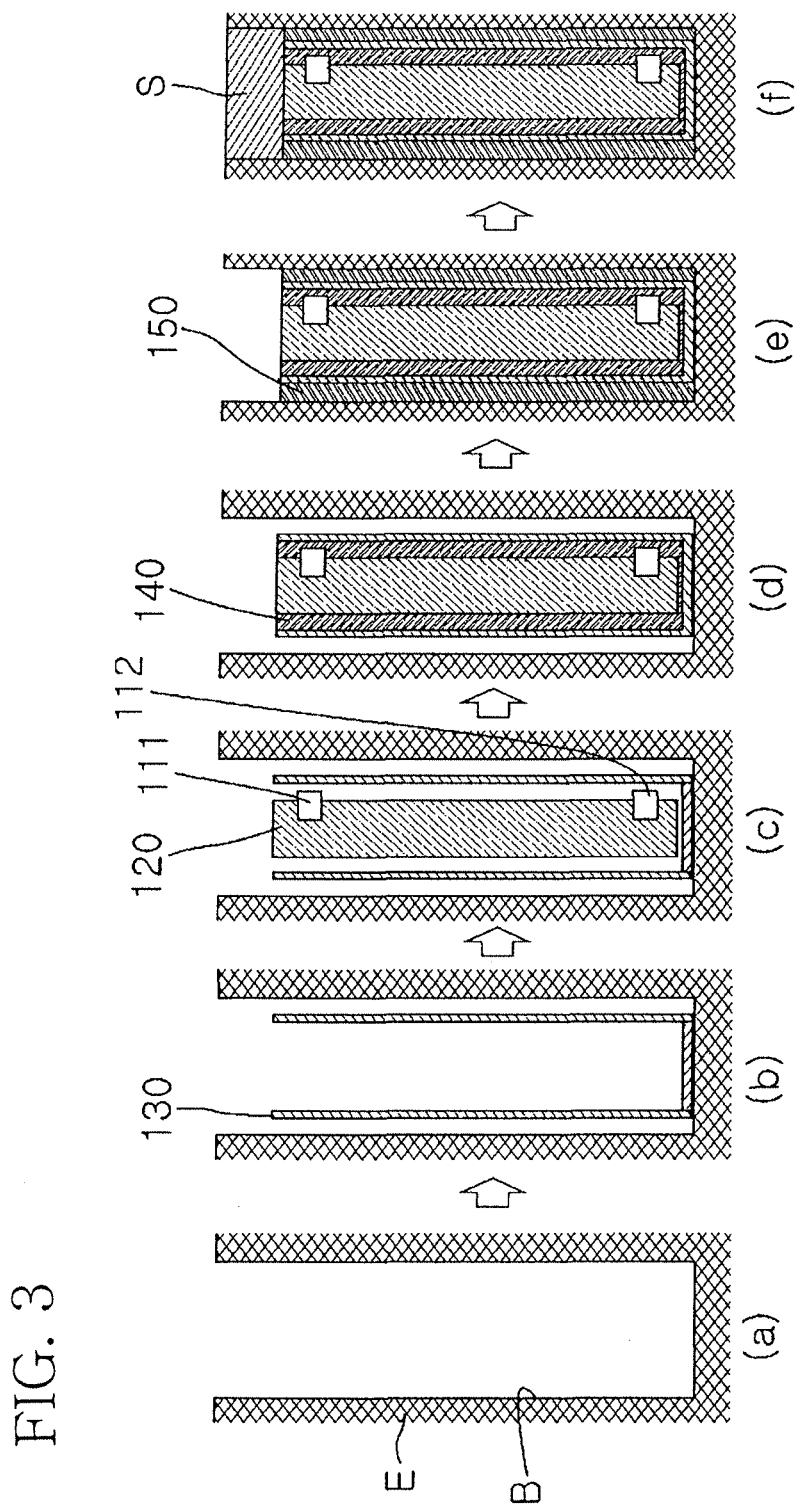
FIG. 3 is a diagram that sequentially shows a producing process of the underground behavior predicting device 100 using the acoustic emission sensor of FIG. 2.

FIG. 3 is a diagram that sequentially shows a producing process of the underground behavior predicting device 100 using the acoustic emission sensor of FIG. 2.

As shown in FIG. 3, the underground behavior predicting device 100 using an acoustic emission sensor may be produced as follows. That is, the waveguide rod 120 having an elongated end to be inserted into a borehole B is produced and a plurality of acoustic emission sensors 111 and 112 are adhered to different positions of the waveguide rod 120.

Subsequently, the wrapping layer 130 is disposed around the waveguide rod 120 to cover the waveguide rod 120. The homogeneous acoustic emission generating layer 140 fills a space between the waveguide rod 120 and the wrapping layer 130 to be cured. Differently from a conventional case that cement grouting is directly performed, the acoustic emission generating layer 140 easily secures a homogeneous material and increases reliability of the acoustic emission.

A lower end of the wrapping layer 130 is sealed with a member such as a sealing cap 131 to block leakage of the acoustic emission generating layer 140 in an uncured state.

The waveguide rod 120 tightly fixed by the acoustic emission generating layer 140 is inserted into the borehole B and is fixed by the grouting layer 150. The grouting layer 150 may be formed of cement. However, since a main agent generating the acoustic emission is the acoustic emission generating layer 140, the reliability of the signal is improved differently from the case that only the grouting layer 150 is used. A surface cap layer S covers from an upper end portion of the waveguide rod 120 to an inlet of the borehole B. The surface cap layer S prevents that acoustic emission due to a shock from a ground is sensed by the first acoustic emission sensor 111 or the second acoustic emission sensor 112.

Figure 4:
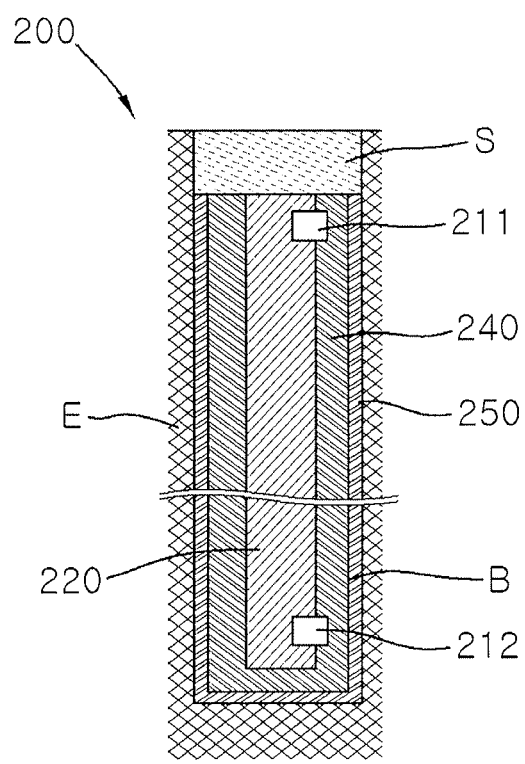
FIG. 4 is a cross-sectional view showing an underground behavior predicting device 200 using an acoustic emission sensor in accordance with another exemplary embodiment.
Figure 5:
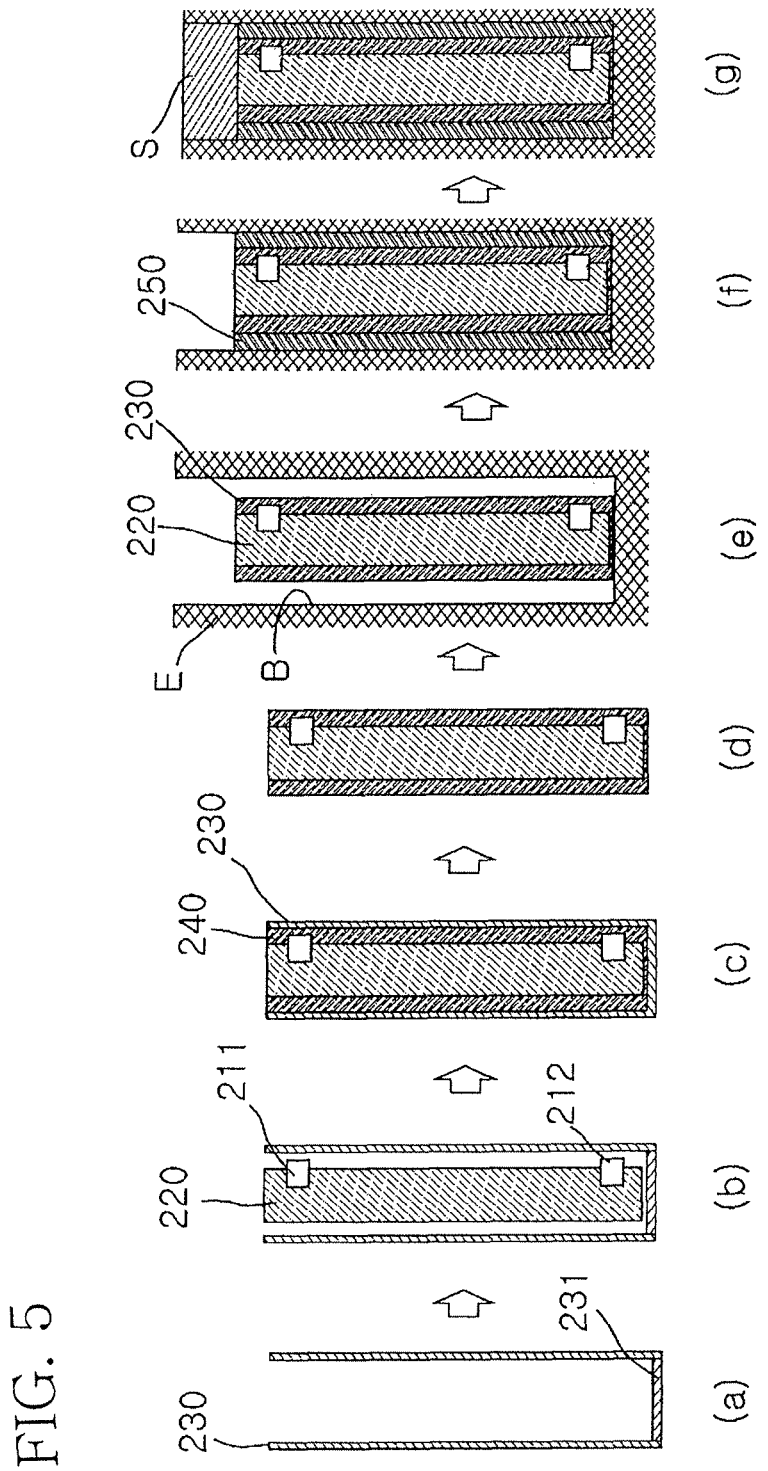
FIG. 5 is a diagram that sequentially shows a producing process of the underground behavior predicting device 200 using the acoustic emission sensor of FIG. 4.

FIG. 4 is a cross-sectional view showing an underground behavior predicting device 200 using an acoustic emission sensor in accordance with another exemplary embodiment. FIG. 5 is a diagram that sequentially shows a producing process of the underground behavior predicting device 200 using the acoustic emission sensor of FIG. 4.

The underground behavior predicting device 200 using the acoustic emission sensor in accordance with another exemplary embodiment includes a waveguide rod 220, a first acoustic emission sensor 211 and the second acoustic emission sensor 212, an acoustic emission generating layer 240 and a grouting layer 250. That is, comparing with the above-mentioned exemplary embodiment, the wrapping layer 130 is removed in this exemplary embodiment. The producing method includes the steps of: producing the waveguide rod 220 having an elongated end to be inserted into a borehole B, mounting a plurality of acoustic emission sensors 211 and 212 on different positions of the waveguide rod 220; disposing the wrapping layer 230 to cover a circumferential surface of the waveguide rod 220 such that a gap is formed between the waveguide rod 220 and the wrapping layer 230; filling and curing the homogeneous acoustic emission generating layer 240 in the formed gap; removing the wrapping layer after curing the acoustic emission generating layer 140; and forming the grouting layer 250 formed on an outside of the wrapping layer 230 to fix the waveguide rod 220 to the borehole B.

The wrapping layer 230 may be configured to include a resin pipe or a releasing agent layer and be removed easily after curing the acoustic emission generating layer 240.

Exemplary Embodiment 1

1. Calculate an estimated breaking face by performing computer analysis.
2. Perform boring sufficiently to penetrate the estimated breaking face. Collect information such as a layer boundary based on boring information.
3. Adhere an AE sensor to a stainless metal body (waveguide rod) to dispose the estimated breaking face and the layer boundary between two acoustic emission sensors.

A metal body is produced to be connected considering that the depths of the borehole varies. A sensor damage that may occur at the time of insertion into the ground is prevented by disposing the metal body at a center of the borehole by using a centralizer, which is an element for disposing the metal body in a center of the borehole, at an inside/outside that the sensor is installed.

4. Insert a wrapping layer pipe having a closed lower end into the borehole. Since the borehole depth may change, it is possible to connect the wrapping layer.
5. Install the metal waveguide rod in the ground to be disposed at a center of the wrapping layer pipe. Arrange a signal line aside.
6. Perform grouting on an epoxy AE generating layer inside the wrapping layer pipe.
7. Perform grouting an outside of the wrapping layer pipe with cement.

The underground behavior predicting devices 100 and 200 using the acoustic emission sensor described above adopts a configuration that the homogeneous the acoustic emission generating layers 140 and 240 cover around the waveguide rods 120 and 220. In the configuration, there is no sieving in a material according to distances and a precise acoustic emission signal is obtained. Also, the wrapping layers 130 and 230 disposed around the waveguide rods 120 and 220 prevents a leakage of the acoustic emission generating layer uncured in the curing process, maintains a regular cured shape, and may be an additional place for emitting acoustic emission with the inner acoustic emission generating layer. It is also possible to simplify the configuration by removing the wrapping layer 230.

It will be apparent to those skilled in the art that the device for predicting underground behavior by using an acoustic emission sensor and the producing method thereof may not be limitedly applied by the configuration and method of the above-mentioned exemplary embodiment. All or the part of the exemplary embodiments may be selectively combined and configured to realize diverse modifications.

What is claimed is:

1. A device for predicting an underground behavior by using an acoustic emission (AE) sensor, comprising:
    a waveguide rod having an elongated end to be inserted in a borehole;
    a plurality of acoustic emission sensors mounted on different positions of the waveguide rod;
    a wrapping layer configured to cover a circumferential surface of the waveguide rod such that a gap is formed between the waveguide rod and the wrapping layer;
    an acoustic emission generating layer filling the gap and being homogeneous along a length of the waveguide rod; and
    a grouting layer configured to fix the waveguide rod in the borehole.

2. The device for predicting an underground behavior by using an acoustic emission sensor of claim 1, wherein the waveguide rod is formed of a metal material.

3. The device for predicting an underground behavior by using an acoustic emission sensor of claim 1, wherein the plurality of acoustic emission sensors comprise a first acoustic emission sensor disposed on an upper end of the waveguide rod and a second acoustic emission sensor disposed on a lower end of the waveguide rod.

4. The device for predicting an underground behavior by using an acoustic emission sensor of claim 1, wherein the wrapping layer is formed of a resin based pipe.

5. The device for predicting an underground behavior by using an acoustic emission sensor of claim 1, wherein the wrapping layer is sealed to block a lower end portion of the waveguide rod and has an open type upper end.

6. The device for predicting an underground behavior by using an acoustic emission sensor of claim 1, wherein the acoustic emission generating layer is formed of epoxy resin.

7. The device for predicting an underground behavior by using an acoustic emission sensor of claim 1, wherein the grouting layer is formed of cement.

8. A device for predicting an underground behavior by using an acoustic emission (AE), comprising:
    a waveguide rod having an elongated end to be inserted in a borehole;
    a first acoustic emission sensor mounted on an upper end of the waveguide rod and a second acoustic emission sensor mounted on an lower end of the waveguide rod;

a cured homogeneous acoustic emission generating layer disposed to cover a circumferential surface of the waveguide rod; and a grouting layer formed on an outside of the cured homogeneous acoustic emission generating layer for fixing the waveguide rod.

9. The device for predicting an underground behavior by using an acoustic emission of claim 8, wherein the acoustic emission generating layer is formed of epoxy resin and the grouting layer is formed of cement.

10. A producing method of a device for predicting an underground behavior by using an acoustic emission (AE), comprising the steps of:

producing a waveguide rod having an elongated end to be inserted in a borehole;

mounting a plurality of acoustic emission sensors on different positions of the waveguide rod;

disposing a wrapping layer to cover a circumferential surface of the waveguide rod such that a gap is formed between the waveguide rod and the wrapping layer;

filling and curing a homogeneous acoustic emission generating layer in the formed gap; and forming a grouting layer, formed on an outside of the wrapping layer, to fix the waveguide rod to the borehole.

11. The producing method of claim 10, wherein the step of disposing the wrapping layer to cover the circumferential surface of the waveguide rod further comprising the step of sealing a lower end of the wrapping layer to block leakage of the acoustic emission generating layer.

12. The producing method of claim 10, wherein the step of mounting the plurality of acoustic emission sensors on different positions of the waveguide rod is preparing a recess on each of a lower end and an upper end of the waveguide rod; mounting a first acoustic emission sensor to a recess of the upper end; and mounting a second acoustic emission sensor to a recess of the lower end.

13. The producing method of claim 10, between the step of filling and curing the homogeneous acoustic emission generating layer in the formed gap and the step of forming the grouting layer formed on the outside of the wrapping layer to fix the waveguide rod to the borehole, further comprising the step of removing the wrapping layer.

* * * * *